Aug. 25, 1953 C. A. LONGMIRE Plant Pat. 1,211
LANTANA PLANT
Filed June 10, 1952
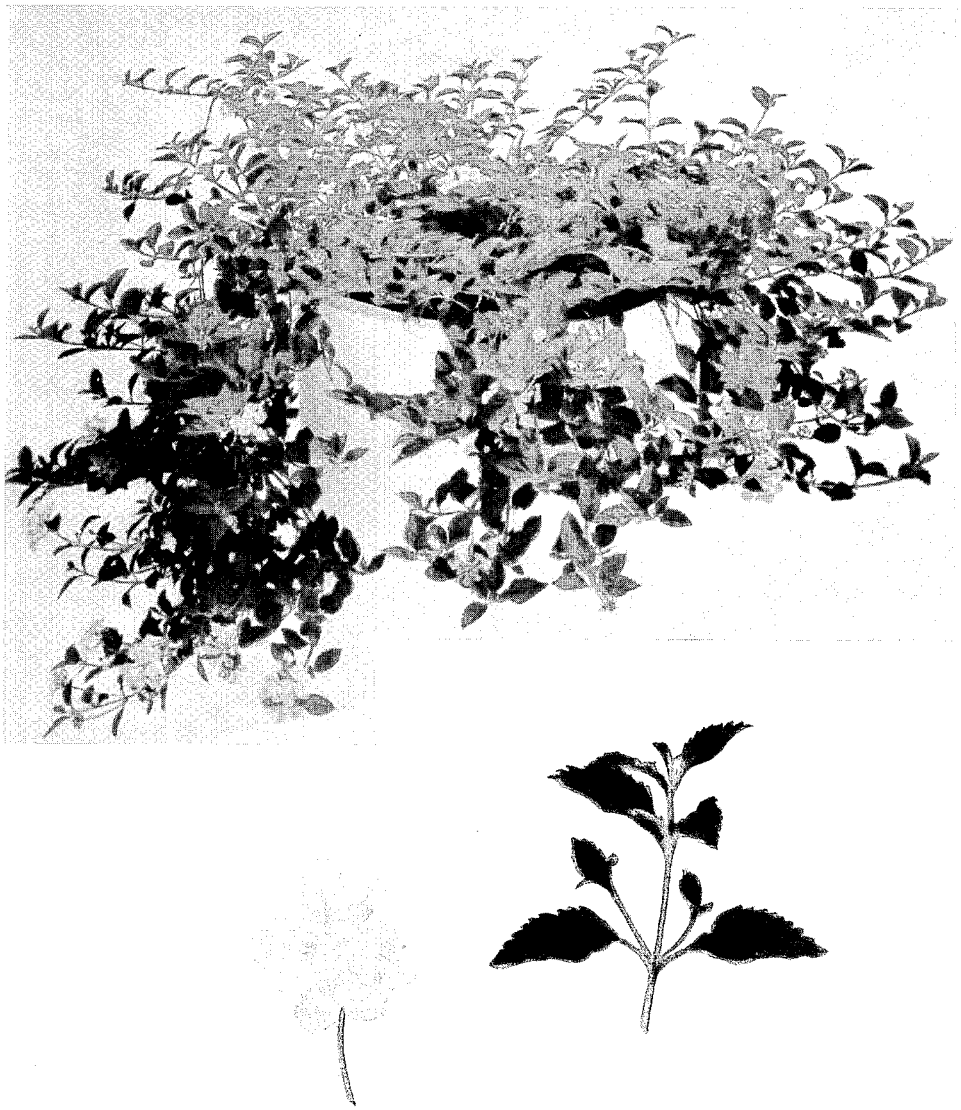
INVENTOR
Charles A. Longmire
By Orville M. Kile
Plant Pat. Agent.

Patented Aug. 25, 1953

Plant Pat. 1,211

UNITED STATES PATENT OFFICE 1,211

LANTANA PLANT

Charles A. Longmire, El Cajon, Calif., assignor to Monrovia Nursery Company, Monrovia, Calif., a corporation of California Application June 10, 1952, Serial No. 292,780

1 Claim. (Cl. 47—60)

My present invention relates to a new and distinct variety or species of lantana plant which resulted from a cross between *L. camara* and *L. sellowiana* (both unpatented) in extensive experiments made by me at my nurseries in Southern California. Since this was a cross between two different species of lantana, a new type, as well as variety, has been produced which combines some of the characteristics of each of the parents. In particular, it has the prostrate growing habit of the *L. sellowiana* type with the flower color of the *L. camara* type, the present variety having a clear yellow flower color.

Accompanying illustrations show a black-and-white photograph of a plant of my new yellow-flowered variety, indicating its prostrate or trailing growth habit; also a separate umbel and leaf-branch of the same variety in full color.

Asexual reproduction of this new variety of lantana has been accomplished by me in Southern California, by means of cuttings and its distinguishing characteristics appear to be permanent. It cannot be reproduced by sexual means, as it does not reproduce true from seed.

Following is a detailed description, wherein color names and numbers refer to the British Horticultural Colour Chart.

*The plant*

Growth habit: Weeping or trailing; spreading and much branched. It forms a prostrate, densely-foliated plant growing from a central root, with vinelike stems to 3 feet in length.

Stems: Slender; vinelike; larger branches four-angled; pubescent.

Leaves: Persistent. Moderate to very dense foliation.

*Size.*—Range from ⅝ to ⅞ inch in width and from 1 to 1¼ inch in length.

*Shape.*—Broadly ovate, with apex acute-aristate and base rounded; serrate.

*Peduncle.*—Short.

*Arrangement.*—Opposite.

*Color.*—Leek Green $8^{58}$.

*Aspect and texture.*—Surface sparsely pubescent; ribs prominent; slightly creased and less leathery than leaves of *L. camara*.

*Scent.*—Characteristic *L. camara* odor.

Blooming habit: Profuse bloomer.

*Flower*

Borne: In nearly globular umbels which are produced on strong, axillary peduncles, chiefly on the new terminal growth. Umbels range from 1 inch to 1½ inches in diameter and are composed of from about 12 to 30 individual florets.

Florets:

*Size.*—Small.

*Color.*—Indian Yellow 6/1.

*Corolla.*—Four to five-lobed; tube pubescent, slender and proportionately long.

*Stamens.*—Four; small.

Bracts: Pubescent; slender; same color as stems; approximately half the length of corolla-tube of floret.

Having thus disclosed my invention, I claim:

The new and distinct variety of lantana plant, substantially as herein shown and described, characterized particularly by its abundance of slightly fragrant flowers, and its combination of the prostrate, trailing growth habit of the *L. sellowiana* and the clear yellow flower coloring of the *L. camara*.

CHARLES A. LONGMIRE.

No references cited.